(12) United States Patent
Lenglet

(10) Patent No.: US 8,289,017 B2
(45) Date of Patent: Oct. 16, 2012

(54) METHOD AND DEVICE FOR ANALYSING A MAGNETIC MATERIAL, AND ANALYSER INCLUDING THE DEVICE

(75) Inventor: Luc Lenglet, Levallois Perret (FR)

(73) Assignee: Magnisense Technology Limited (CY)

( * ) Notice: Subject to any disclaimer, the term of this patent is extended or adjusted under 35 U.S.C. 154(b) by 394 days.

(21) Appl. No.: 12/676,405

(22) PCT Filed: Sep. 5, 2008

(86) PCT No.: PCT/IB2008/055606
§ 371 (c)(1),
(2), (4) Date: Apr. 22, 2010

(87) PCT Pub. No.: WO2009/031129
PCT Pub. Date: Mar. 12, 2009

(65) Prior Publication Data
US 2010/0301850 A1 Dec. 2, 2010

Related U.S. Application Data

(60) Provisional application No. 60/970,678, filed on Sep. 7, 2007.

(30) Foreign Application Priority Data

Sep. 7, 2007 (FR) ...................................... 07 57437

(51) Int. Cl.
*G01N 27/72* (2006.01)
(52) U.S. Cl. ........................................ 324/228; 324/234
(58) Field of Classification Search .................. 324/219, 324/228, 234
See application file for complete search history.

(56) References Cited

U.S. PATENT DOCUMENTS

| | | | |
|---|---|---|---|
| 2003/0027197 A1 | 2/2003 | Nikitin et al. | |
| 2007/0155024 A1* | 7/2007 | Miethe et al. | 436/524 |
| 2008/0252289 A1 | 10/2008 | Lenglet et al. | |
| 2008/0261329 A1 | 10/2008 | Nikitin et al. | |

FOREIGN PATENT DOCUMENTS

| | | |
|---|---|---|
| DE | 101 26 940 A1 | 12/2002 |
| EP | 1 262 766 A2 | 12/2002 |
| WO | WO 2004/077044 | 9/2004 |

(Continued)

OTHER PUBLICATIONS

Zhang, et al., "Design of nanostructured biological materials through self-assembly of peptides and proteins", Current Opinion in Chemical Biology 2002, 6:865-871.

(Continued)

*Primary Examiner* — Bot Ledynh
(74) *Attorney, Agent, or Firm* — Cantor Colburn LLP

(57) ABSTRACT

Disclosed is a method of analysing a magnetic material which includes the construction of a signature S(H) of the magnetic material formed from at least two points $S(H)_P$, this construction including obtaining the value of each point $S(H)_P$ by measuring, over each period fraction, the amplitude and possibly the phase of a harmonic of the magnetic field induced in the magnetic material, said amplitude and phase being obtained in response only to an excitation during this period fraction, the harmonic having a frequency $nf_H$, where n is a non-zero positive integer; and the identification and/or the determination of the mass of the magnetic material from several points of the constructed signature S(H).

19 Claims, 6 Drawing Sheets

FOREIGN PATENT DOCUMENTS

WO  WO 2009/031129 A2  3/2009

OTHER PUBLICATIONS

Reches, et al., "Molecular Self-Assembly of Peptide Nanostructures: Mechanism of Association and Potential Uses", Current Nanoscience, 2006, 2, 105-111.

Bao, et al., "An Array of Concentric Composite Nanostructure of Metal Nanowires Encapsulated in Zirconia Nanotubes: Preparation, Characterization, and Magnetic Properties", Chem. Mater. 2002, 14, 4709-4713.

Banerjee, et al., "Cu nanocrystal growth on peptide nanotubes by biomineralization: Size control of Cu nanocrystals by tuning peptide conformation", PNAS, Dec. 9, 2003, vol. 100, No. 25, 14678-14682.

Zhao, et al., "Simultaneous Targeted Immobilization of Anti-Human IgG-Coated Nanotubes and Anti-Mouse IgG-Coated Nanotubes on the Complementary Antigen-Patterned Surfaces via Biological Molecular Recognition", J. Am. Chem. Soc., 2005, 127, 8930-8931.

Banerjee, et al., "Magnetic Nanotube Fabrication by Using Bacterial Magnetic Nanocrystals", Adv. Mater. 2005, 17, 1128-1131.

Bittner, "Biomolecular rods and tubes in nanotechnology", Naturwissenschaften, 2005, 92:51-64.

Hong et al., "Magnetic susceptibility reduction method for magnetically labeled immunoassay", Applied Physics Letters, May 26, 2006, pp. 212512 (1-3), vol. 88, Am. Instit. Phy.

Krause et al., "Magnetic particle detection by frequency mixing for immunoassay applications", Journal of Magnetism and Magnetic Materials, 311 (2007) 436-444.

* cited by examiner

METHOD AND DEVICE FOR ANALYSING A MAGNETIC MATERIAL, AND ANALYSER INCLUDING THE DEVICE

CROSS REFERENCE TO RELATED APPLICATIONS

This application claims priority to U.S. provisional patent 60/970,678, filed Sep. 7, 2007, and French patent application, FR 07 57437 filed Sep. 7, 2007, both herein incorporated by reference.

The present invention relates to a method and a device for analysing a magnetic material, and to an analyser that includes the device.

There are methods for measuring the mass of a magnetic material that comprise:
 a) excitation of the magnetic material simultaneously with:
   a low-frequency excitation magnetic field of periods $T_L$, the period $T_L$ comprising at least first and second period fractions such that the average of the instantaneous value of the low-frequency magnetic field over the first period fraction is different from the average of its instantaneous value over the second period fraction, each period fraction having a duration of at least 100 nanoseconds and
   a high-frequency excitation magnetic field, the variation of the instantaneous value of which over the course of time is periodic with a frequency $f_H$, the frequency $f_H$ of the high-frequency excitation magnetic field being at least two times the frequency $f_L$ of the low-frequency magnetic field.

Such a method is described for example in EP 1 262 766 for measuring the quantity of magnetic particles in an analysis medium. This method works particularly well.

However, it is now desirable to be able to measure the mass of magnetic material, for example present in an analysis medium, with greater sensitivity.

One subject of the invention is therefore a method of measuring the mass of a magnetic material, in which the method also comprises:
 b) the construction of a signature $S(H)$ of the magnetic material formed from at least two points $S(H)_P$, this construction including obtaining the value of each point $S(H)_P$ by measuring, over each period fraction, the amplitude of a harmonic of the magnetic field induced in the magnetic material, said amplitude being obtained in response to the excitation during this period fraction, the harmonic having a frequency $nf_H$, where n is a non-zero positive integer; and
 c) the identification and/or the determination of the mass of the magnetic material from several points of the constructed signature $S(H)$.

It may be shown that the signature $S(H)$ is approximately equal to the n-th derivative of the magnetic induction B (Tesla) with respect to the magnetic field H (Ampere per meter). The following equation can therefore be written:

$$S(H) = \frac{d^n B(H)}{dH^n} \quad (1)$$

where B is the magnetic induction as a function of the magnetic field H.

EP 1 262 766 indicates that it is possible to isolate the amplitude of the harmonic of frequency $nf_H$. However, to do this, only the mean effect of the measurements made of several periods $T_L$ of the low-frequency magnetic field is used. Under these conditions, the measured amplitude $S(0)$ is approximately equal to $d^n B(0)/dH^n$, that is to say approximately equal to the value of the n-th derivative of the induction B with respect to the magnetic field for a zero field. Thus, the quantity of magnetic particles in the analysis medium is determined only from the point $S(0)$.

However, in the above measurement method, the amplitude of the harmonic of frequency $nf_H$ is measured alternately over first and second fractions of the period $T_L$. The first and second period fractions are chosen here so that the mean of the instantaneous value of the low-frequency magnetic field over the first period fraction is different from the mean of the instantaneous value of the same field over the second period fraction. Here we denote $H_1$ and $H_2$ as the means of the instantaneous value of the low-frequency magnetic field over the first and second period fractions respectively. The amplitudes of the harmonic of frequency $nf_H$ over the first and second period fractions are approximately equal to $d^n B(H_1)/dH^n$ and $d^n B(H_2)/dH^n$, respectively. The values of $d^n B(H_1)/dH^n$ and $d^n B(H_2)/dH^n$ are denoted here by $S(H_1)$ and $S(H_2)$, respectively.

Thus, the constructed signature $S(H)$ is composed of at least two points $S(H_1)$ and $S(H_2)$. As in EP 1 262 766, the value of each of these points is representative of the mass of magnetic material present in the analysis medium. However, in the above method, at least two points $S(H_1)$ and $S(H_2)$ of the signature $S(H)$ are used to identify or determine the mass of the magnetic material. The use of two points $S(H_1)$ and $S(H_2)$ of the signature $S(H)$ improves the noise immunity compared with the case in which only a single point $S(0)$ of the amplitude is used.

In addition, using at least two points of the signature $S(H)$, it becomes easier to discriminate between magnetic materials having different signatures and therefore to identify the magnetic materials using the above method.

The embodiments of this method may include one or more of the following features:
 a) the automatic identification of the magnetic material as a function of the result of the correlation of the signature $S(H)$ with each of the reference signatures $S_{ref}(H)_i$ of a set of several reference signatures, each reference signature $S_{ref}(H)_i$ having been obtained with a magnetic material different from the other magnetic materials used to obtain the other reference signatures, first and second magnetic materials being considered as different from each other if an intercorrelation coefficient $\beta$ defined by the following equation is less than 0.95:

$$\beta = \frac{\left| \oint_H \frac{d^n B(H)_1}{dH^n} \frac{d^n B(H)_2}{dH^n} dH \right|}{\sqrt{\left( \oint_H \left(\frac{d^n B(H)_1}{dH^n}\right)^2 dH \right) \left( \oint_H \left(\frac{d^n B(H)_2}{dH^n}\right)^2 dH \right)}}$$

where:

$$\frac{d^n B(H)_1}{dH^n} \text{ and } \frac{d^n B(H)_2}{dH^n}$$

are the n-th derivatives of the magnetic induction with respect to the magnetic field of the first and second magnetic materials respectively, n being the same number as that defining the harmonic of frequency $nf_H$; and $$-\oint_H dH$$

indicates that the integration is carried out, in the same manner for both the first and second magnetic materials, by circulation over a closed path, describing a cycle starting from $H_{min}$, passing through $H_{max}$ and returning to $H_{min}$, where $H_{min}$ and $H_{max}$ are the minimum and maximum of the excitation magnetic field respectively;

b) the determination of the mass comprises:

the multiplication of several points of the signature S(H) with, respectively, each corresponding point of a reference signature $S_{ref}(H)_i$ measured under the same conditions on a reference mass of the same magnetic material; and the calculation of the mass of the homogeneous magnetic material as a function of the result of this multiplication;

c) the identification and/or the determination of the mass of the magnetic material are/is also carried out on the basis of at least one reference signature $S_{ref}(H)_i$ measured under the same conditions on a reference mass of the same magnetic material;

d) the construction of the signature S(H) of the magnetic material comprises obtaining the value of each point $S(H)_p$ by measuring, over each period fraction, the amplitude and the phase of a harmonic of the magnetic field induced in the magnetic material, said amplitude and phase being obtained in response to the excitation during this period fraction;

These embodiments of the method also have the following advantages:

using the result of the correlation of the signature S(H) with each of the reference signatures $S_{ref}(H)_i$ allows a mass of magnetic material to be identified automatically and reliably; and multiplying the signature S(H) by a reference signature $S_{ref}(H)_i$ point by point helps to improve the signal-to-noise ratio and therefore the sensitivity of the method.

The subject of the invention is also the above method applied to the analysis of an assembly of several different magnetic materials, first and second magnetic materials being considered as different from each other if an intercorrelation coefficient β defined by the following equation is less than 0.95:

$$\beta = \frac{\left[\oint_H \frac{d^n B(H)_1}{dH^n} \frac{d^n B(H)_2}{dH^n} dH\right]}{\sqrt{\left(\oint_H \left(\frac{d^n B(H)_1}{dH^n}\right)^2 dH\right)\left(\oint_H \left(\frac{d^n B(H)_2}{dH^n}\right)^2 dH\right)}}$$

where:

$$-\frac{d^n B(H)_1}{dH^n} \text{ and } \frac{d^n B(H)_2}{dH^n}$$

are the n-th derivatives of the magnetic induction with respect to the magnetic field of the first and second magnetic materials respectively, n being a non-zero positive integer; and $$-\oint_H dH$$

indicates that the integration is carried the same way for the first and the second magnetic materials, through circulation on a closed path forming a cycle starting from $H_{min}$, going through $H_{max}$ and coming back to $H_{min}$, wherein $H_{min}$ and $H_{max}$ are the minimum and the maximum respectively of the excitation magnetic field, in which the identification and/or the determination (90) consist/consists in identifying and/or determining the mass of at least one of the magnetic materials of the assembly on the basis of several points of the signature S(H) and of several signatures $S_{ref}(H)_i$, each measured under the same conditions on a reference mass of each of the magnetic materials of the assembly.

According to the invention, the word assembly means only the presence of the different magnetic materials. These materials may be linked or not and/or present in a same solid or liquid phase.

The above method has the advantage of enabling the mass of a specific magnetic material to be identified in an assembly of several different magnetic materials and to be measured.

The embodiments of this method of analysing an assembly of magnetic materials may include the following feature:

the determination of the masses of each of the magnetic materials in the assembly of magnetic materials comprises the solution of the following matrix equation:

$$\begin{bmatrix} S(H)_1 \\ S(H)_2 \\ \vdots \\ S(H)_P \end{bmatrix}^T = \begin{bmatrix} \alpha_1 \\ \alpha_2 \\ \vdots \\ \alpha_Q \end{bmatrix}^T \begin{bmatrix} S_{ref}(H)_{11} & \cdots & S_{ref}(H)_{1P} \\ S_{ref}(H)_{21} & \cdots & S_{ref}(H)_{2P} \\ \vdots & & \vdots \\ S_{ref}(H)_{Q1} & \cdots & S_{ref}(H)_{QP} \end{bmatrix} + \begin{bmatrix} N(H)_1 \\ N(H)_2 \\ \vdots \\ N(H)_P \end{bmatrix}^T$$

where:

Q is the number of reference signatures, Q being equal to or greater than the number of different magnetic materials present in the assembly;

P is the number of points of each signature, P being equal to or greater than two;

$S(H)_j$ is the j-th point of the signature S(H);

$\alpha_i$ is the ratio of the mass to be measured, of the magnetic material having the signature $S_{ref}(H)_i$, to the reference mass used to construct the signature $S_{ref}(H)_i$;

$S_{ref}(H)_{ij}$ is the j-th point of the signature $S_{ref}(H)_i$;

$N(H)_j$ is the j-th point of a signal representative of the noise added to the measurement of the signature S(H); and "$T$" is the symbol for the transpose function.

This embodiment of the method of analysing an assembly of magnetic materials also has the following advantage:

solving the above matrix equation allows the mass of each of the magnetic materials contained in the assembly to be obtained simultaneously.

The embodiments of these methods of analysis may also include the following feature:

the instantaneous value of the low-frequency magnetic field during each of the period fractions is constant.

The subject of the invention is also a device for analysing a magnetic material, comprising:

a) a generator designed to excite the magnetic material simultaneously with:

a low-frequency excitation magnetic field of periods $T_L$, the period $T_L$ comprising at least first and second period fractions such that the average of the instantaneous value of the low-frequency magnetic field over the first period fraction is different from the average of its instantaneous value over the second period fraction, each period fraction having a duration of at least 100 nanoseconds and a high-frequency excitation magnetic field, the variation of the instantaneous value of which over the course of time is periodic with a frequency $f_H$, the frequency $f_H$ of the high-frequency excitation magnetic field being at least two times the frequency $f_L$ of the low-frequency magnetic field, the device also comprises:

b) a signature constructor for constructing a signature S(H) of the magnetic material formed from at least two points $S(H)_P$, this constructor being capable of obtaining the value of each point $S(H)_P$ by measuring, over each period fraction, the amplitude and possibly the phase of a harmonic of the magnetic field induced in the magnetic material, said amplitude and phase being obtained in response to the excitation during this period fraction, the harmonic having a frequency $nf_H$, where n is a non-zero positive integer; and c) a module for identifying and/or determining the mass of the magnetic material on the basis of several of the points of the constructed signature S(H).

In a first particular embodiment of the invention, applied to the detection or quantification of a biological or chemical component in a specimen, the assembly is obtained in the following manner:

a first magnetic material, attached to which is a ligand capable of binding the biological or chemical component to be detected, is mixed with the specimen to be analysed, producing a magnetic material/component complex;

the magnetic complex is concentrated in a prescribed volume using a magnetic field;

the complex is then brought into contact with a second, different, magnetic material, attached to which is a ligand also capable of binding the same biological or chemical component to be detected that is present on the first material or to a reactant allowing this component to be detected and/or quantified;

the analysis of the assembly of magnetic materials thus obtained allowing the detection and/or the quantification of this component.

In a second particular embodiment of the invention, applied to the detection or quantification of at least two biological or chemical components in a specimen, the assembly is obtained mixing the specimen:

with a first magnetic material, which binds to a first biological or chemical component or to a reactant allowing this component to be detected and/or quantified;

and with a second, different, magnetic material, which binds to a second biological or chemical component or to a reactant allowing this component to be detected and/or quantified.

In a third particular embodiment of the invention, applied to the detection or quantification of at least two biological or chemical components in a specimen, the assembly is obtained by mixing the specimen:

with a first magnetic material, which binds to the biological or chemical component to be quantified or to a reactant for allowing this component to be detected and/or quantified; and with a second, different, magnetic material, which is inert with respect to the aforementioned component.

The subject of the invention is also the above device applied to the analysis of an assembly of different magnetic materials, in which the identification and/or determination module is capable of identifying and/or determining the mass of at least one of the magnetic materials of the assembly on the basis of several of the points of the constructed signature S(H) and of several signatures $S_{ref}(H)_i$, each measured under the same conditions on a reference mass of each of the magnetic materials of the assembly.

Finally, the subject of the invention is an analyser for analysing an analysis medium that may contain at least one biological and/or chemical component, the material to be analysed including magnetic particles bound to the component or to a reactant for allowing the component to be detected and/or quantified, this analyser comprising:

a receptacle suitable for containing the analysis medium; and a device for measuring the mass of the ensemble of magnetic particles present in the analysis medium, the result of this measurement being proportional to the quantity of component to be analysed that is present in the analysis medium.

In one embodiment, the analyser is intended to analyse an analysis medium containing at least two different magnetic materials. In particular, it may be designed to implement the various modes of application to the detection or quantification of the aforementioned biological or chemical components.

The invention will be more clearly understood on reading the following description, given solely by way of non-limiting example and with reference to the drawings in which.

In these figures, the same references are used to denote the same elements.

In the rest of this description, the features and functions that are well known to those skilled in the art will not be described in detail.

In addition, two magnetic materials are defined here to be identical to each other if an intercorrelation coefficient $\beta$ defined by the following equation is greater than a:

$$\beta = \frac{\left[\oint_H \frac{d^n B(H)_1}{dH^n} \frac{d^n B(H)_2}{dH^n} dH\right]}{\sqrt{\left(\oint_H \left(\frac{d^n B(H)_1}{dH^n}\right)^2 dH\right)\left(\oint_H \left(\frac{d^n B(H)_2}{dH^n}\right)^2 dH\right)}}$$

where:

$$-\frac{d^n B(H)_1}{dH^n} \text{ and } \frac{d^n B(H)_2}{dH^n}$$

are the n-th derivatives of the magnetic induction B with respect to the magnetic field H of the first and second magnetic materials respectively, n being the same integer denoting a harmonic of frequency $nf_H$ in the magnetic field induced in the magnetic material to be analysed; and $$-\oint_H dH$$

indicates that the integration is carried out, in the same manner for both the first and second magnetic materials, by circulation over a closed path, describing a cycle starting from $H_{min}$, passing through $H_{max}$ and returning to $H_{min}$, where $H_{min}$ and $H_{max}$ are the minimum and maximum of the excitation magnetic field respectively.

Two magnetic materials are also considered to be different from each other if this coefficient β is less than a.

The value of a is between 0.5 and 0.95. Preferably, it is between 0.85 and 0.95, for example equal to 0.9 or 0.95. In the embodiment that follows, the value of a is taken to be equal to 0.95.

Figure 1:
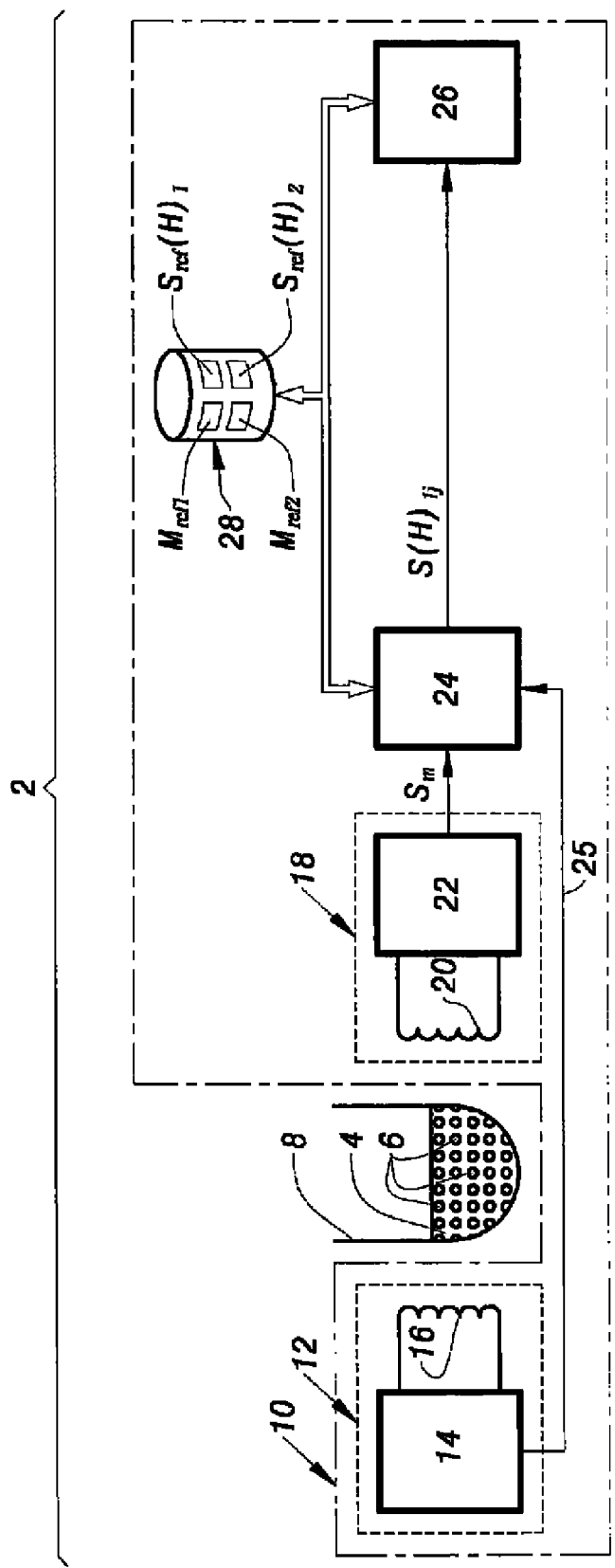
FIG. 1 is a schematic illustration of the architecture of an analyser for analysing a mixture of biological and/or chemical components present in an analysis medium.

FIG. 1 shows an analyser 2 for analysing an analysis medium 4 that may contain at least one biological and/or chemical component.

The analysis medium contains magnetic particles 6 bound to the component or to a reactant for allowing the component to be detected or quantified. This reactant may be a reactant binding to the component. This reactant may be an analogue of the component, capable of competing with the component in a reaction of binding with another element present.

In this example, it will be assumed that the chemical or biological component to be analysed is bound to magnetic particles. These magnetic particles have a non-linear magnetic cycle B(H) for an excitation magnetic field whose value varies between $H_{min}$ and $H_{max}$. The term "magnetic cycle" is understood here to mean the curve representing the variation of the magnetic induction B in the magnetic particles as a function of the value of the excitation magnetic field H.

In this example, the magnetic particles are beads 6 of a superparamagnetic material. These beads have a largest diameter typically between 1 and 100 manometers. The superparamagnetic materials used here are, for example, the same as those described in the patent application filed under FR 05 10278. The magnetic cycle of these superparamagnetic materials also exhibits strong non-linearity for a zero excitation magnetic field. This strong non-linearity is manifested by the presence of an extremum for a zero magnetic field in the third derivative of the magnetic induction with respect to the magnetic field. This extremum is, in absolute value, the largest of the extrema of the third derivative of the magnetic induction.

The population of beads 6 forms a magnetic material called, for simplicity, "magnetic material 6".

The analyser 2 comprises a receptacle 8 for containing the analysis medium 4 and a device 10 for analysing the magnetic material contained in the medium 4.

The term "analysis medium" is understood to mean a delimited zone of the receptacle that is read by the measurement device.

To give an example, the receptacle may be a miniature column filled with porous material(s) or a test strip having at least one porous material, optionally contained in a package. Such receptacles are commonly used in fields of diagnostics and contaminant measurement and research (see for example EP 1 262 766).

The device 10 comprises an excitation magnetic field generator 12 designed to create a magnetic induction in the material 6.

For example, this generator 12 is formed from a current source 14 connected to a coil 16. The source 14 is able to generate an electric current formed by the superposition of a low-frequency signal and a high-frequency signal. For example, the low-frequency signal here is a staircase periodic signal, whereas the high-frequency signal is a sinusoid. The low-frequency signal has a frequency $f_L$ at least ten times lower than the frequency $f_H$ of the high-frequency signal. Typically, the frequency $f_H$ is between 1 kHz and 10 MHz.

The coil 16 converts this electrical signal into an excitation magnetic field close to the material 6. The resulting excitation magnetic field is formed by the superposition of a low-frequency excitation magnetic field $H_L$ and a high-frequency excitation magnetic field $H_H$, created by the low-frequency electrical signal and the high-frequency electrical signal respectively.

Figure 2:
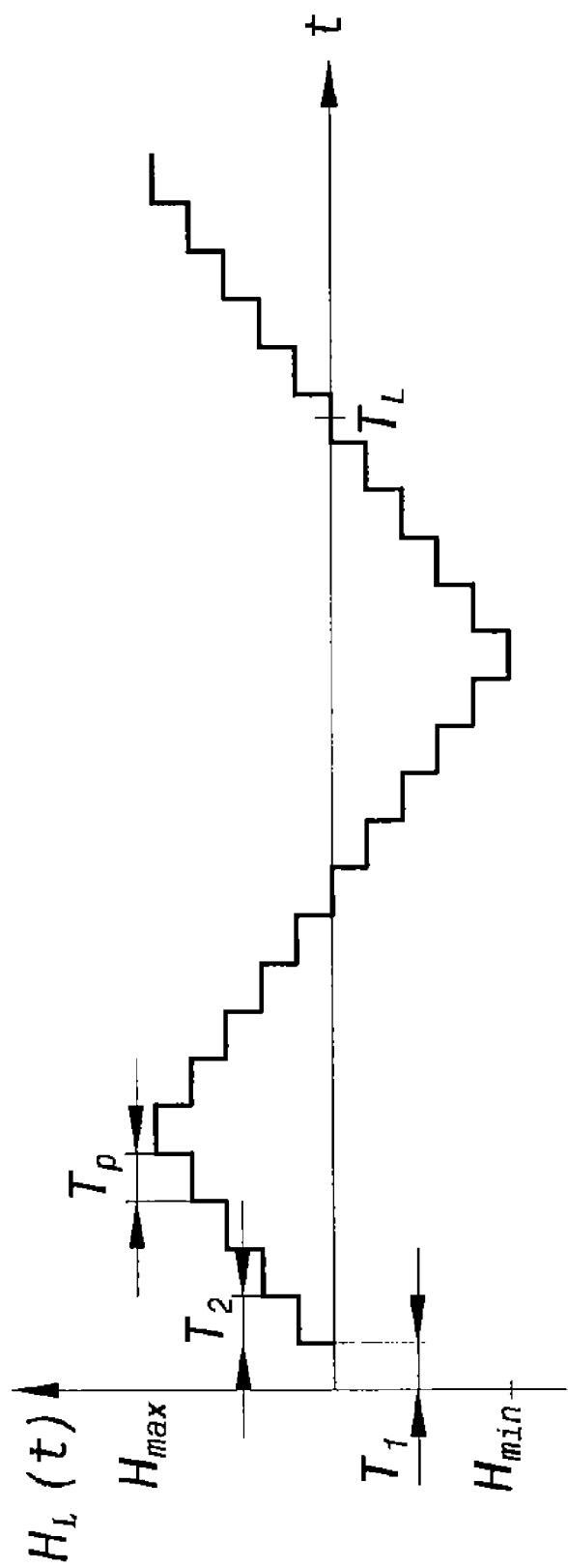
FIG. 2 is a timing diagram showing the waveform of a low-frequency magnetic field used in the analyser of FIG. 1.

FIG. 2 shows the variation of the instantaneous value of the magnetic field $H_L$ over the course of time.

Each period $T_L$ of the magnetic field $H_L$ is divided here into r fractions $T_P$ of the same duration. r is an integer equal to or greater than 2. Here, the magnetic material present in the receptacle 8 has to be identified, the number r has to be equal to or greater than 3 and preferably equal to or greater than 20. If this is not the case, that is to say there is no need to identify the magnetic material, the number r may be equal to 2. To give an illustration, here the number r is equal to 20.

Over each fraction $T_P$, the instantaneous value of the field $H_L$ is constant and denoted by $H_{Li}$. Thus, during the first fraction $T_1$ of the period $T_L$, the instantaneous value of the magnetic field $H_L$ is constant and equal to $H_{L1}$. During the second fraction $T_2$, the instantaneous value of the magnetic field $H_L$ is constant and equal to $H_{L2}$. During a period $T_L$, the value of the magnetic field $H_L$ here takes eleven different values $H_{Li}$ lying between $H_{min}$ and $H_{max}$.

Each fraction $T_P$ lasts at least 100 nanoseconds. Typically, the duration of a fraction $T_P$ is between 100 nanoseconds and 10 seconds and preferably between 1 microsecond and 10 seconds.

The excitation magnetic field $H_H$ is sinusoidal and has a frequency $f_H$.

The device 10 also includes a sensor 18 for detecting the magnetic induction B created in the material 6. For example, the sensor 18 measures the magnetic field created by the magnetic induction B in the material 6 and generates a corresponding measurement signal $S_m$. For example, the sensor 18 comprises a measurement coil 20 connected to the input of an analogue to digital converter 22. The sensor 18 may be replaced with other sensors, such as for example a Hall-effect sensor, a SQUID (Superconducting Quantum Interference Device), a GMR (Giant MagnetoResistive) device or an AMR (Anisotropic MagnetoResistive) device.

Finally, the device 10 includes a signature constructor 24 for constructing a signature S(H) and a module 26 for identifying and determining the mass of the material 6.

The constructor 24 is capable of measuring the amplitude of a harmonic of the magnetic induction in the material 6 obtained in response only to the excitation during a single period fraction $T_P$. Each measurement during a fraction $T_P$ forms a point $S(H)_{1P}$ of the signature S(H) of the magnetic material.

The constructor 24 is connected to a memory 28 for recording the various points of the signature S(H) in this memory. The constructor 24 is also connected to the generator 12 via a link 25 so as to be synchronized with this generator. Finally, the constructor 24 is connected to an input of the module 26.

The module 26 is capable, on the basis of several points of the signature S(H), of identifying the magnetic material and of determining the mass of magnetic material present in the analysis medium 4. For this purpose, the module 26 is also connected to the memory 28.

The memory 28 contains reference signatures $S_{ref}(H)_1$ and $S_{ref}(H)_2$ and reference masses $M_{ref1}$ and $M_{ref2}$ used to obtain these reference signatures.

The operation of the analyser 2 will now be described in greater detail with regard to the method shown in FIG. 3 in the particular case in which the particles 6 are all made of the same magnetic material.

The method is applied to the detection and/or quantification of a biological and/or chemical component (analyte) that may be present in a medium. The analysis medium is therefore a specimen or a fraction of a specimen of the medium to be tested that has been brought into the presence of the magnetic particles or of a reactant or an analogue bound to these particles. According to a preferred mode of operation, the mass of magnetic material that is concentrated with a fraction of the analysis medium in a delimited zone of the receptacle, usually called a reaction zone or detection zone in the diagnostics or contaminant search fields, is determined. The receptacle may be as defined above. The magnetic material may be concentrated in the delimited zone by immobilizing the analyte and/or possible binding partners or reactants, in the presence of magnetic beads specifically bound to one of these elements, on a ligand, especially a ligand immobilized on a solid support in the detection zone. As is known per se in particular in the diagnostics field, the reaction may be of the sandwich, blocking or competition type.

To give an example, in a sandwich-type test, intended to detect and quantify an antigen, the analyte is the antigen, the reactant is a labelled antibody, that is to say one bound to the magnetic particles, and the ligand is a specific antibody for the antigen. The analyser detects the signal emitted by the reactant bound to the analyte, which is itself bound to the ligand.

It will also be assumed that the magnetic material used to produce the beads 6 is chosen from the group composed only of two different magnetic materials, called type 1 magnetic material and type 2 magnetic material respectively.

Figure 4:
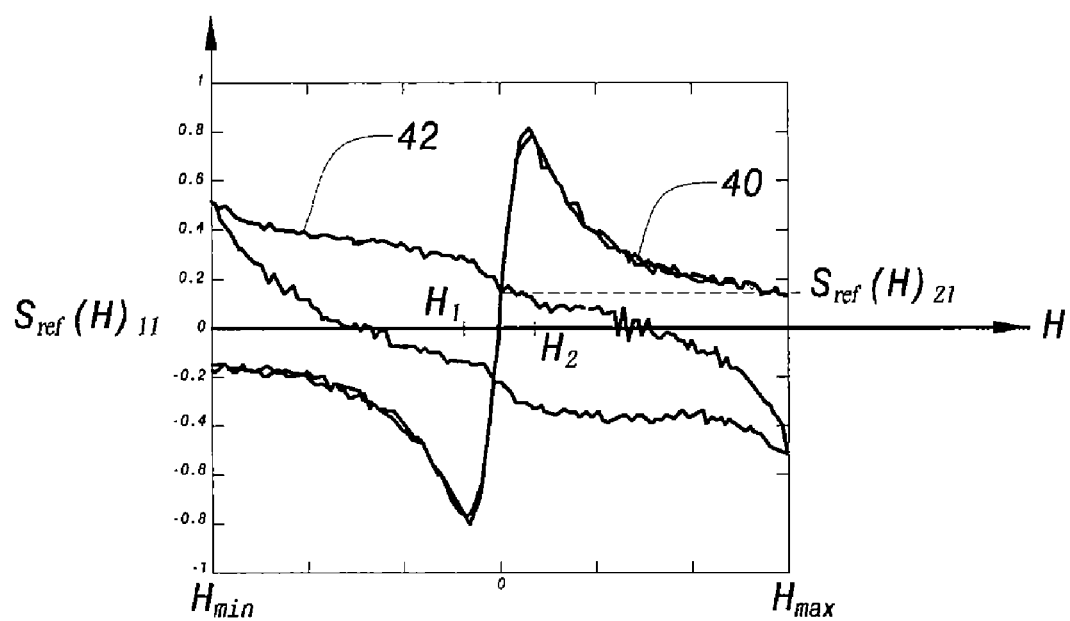
FIG. 4 is a graph illustrating the second derivative of the magnetic induction with respect to the magnetic field for two different magnetic materials.

FIG. 4 shows, by a curve 40, the variation of the second derivative of the magnetic induction B as a function of the magnetic field H for the type 1 magnetic material between the values $H_{min}$ and $H_{max}$. Here, the type 1 magnetic material is a superparamagnetic material. More precisely, this material is formed from beads called "SeraMag® Magnetic particles" supplied by Seradyn, Inc. These beads have the reference "3075050255 SeraMag® Magnetic Carboxylate-Modified Ferrofluid". This type 1 magnetic material exhibits practically no hysteresis. In addition, the curve 40 has a minimum for an excitation magnetic field equal to $H_1$.

The curve 40 also has a maximum for an excitation magnetic field equal to $H_2$.

FIG. 4 also shows the variation of the second derivative of the magnetic induction with respect to the magnetic field for the type 2 magnetic material in the form of a curve 42 between the values $H_{min}$ and $H_{max}$.

This type 2 magnetic material is for example formed from MagPrep® particles supplied by Merck KGaA and bearing the reference 1.01193.0050 "Silica particles MagPrep®".

Unlike the type 1 magnetic material, the type 2 magnetic material exhibits hysteresis.

The method of analysing the magnetic material 6 firstly starts with a phase 36 of calibrating the device 10.

During phase 36, in a step 38, a known reference mass $M_{ref1}$ of the type 1 magnetic material is placed in the receptacle 8.

Next, in a step 44, the generator 10 excites the magnetic material placed in the receptacle 8 simultaneously with the magnetic fields $H_L$ and $H_H$. This results in an excitation magnetic field whose power spectrum has two peaks that dominate all the other peaks at the frequencies $f_L$ and $f_H$ respectively. In response to this excitation magnetic field, a magnetic induction appears in the various particles of the type 1 magnetic material that is placed in the receptacle 8. The magnetic induction results in the creation of a magnetic field that can be measured by the sensor 18. This magnetic field created by the magnetic induction in the type 1 magnetic materials has harmonics at the multiple integers of the frequency $f_H$. The appearance of these harmonics is due to the non-linearities of the magnetic cycle B(H) of the type 1 magnetic material.

In parallel, in a step 46, the sensor 18 measures the magnetic field resulting from the magnetic induction created within the type 1 magnetic material. A corresponding measurement signal $S_m$ is then sent to the signature constructor 24.

Next, in a step 48, the constructor 24 constructs the signature $S_{ref}(H)_1$. To do this, the constructor constructs, on the basis of only the measurements made by the sensor 18 during the fraction $T_1$, the first point $S_{ref}(H)_{11}$ of the signature $S_{ref}(H)_1$. Here, the constructor measures the amplitude and the phase of the harmonic of frequency $2f_H$. Over this fraction $T_1$, the amplitude of the harmonic of frequency $2f_H$ is approximately equal to the absolute value of $S_{ref}(H)_{11}$. The phase of this harmonic gives the sign of $S_{ref}(H)_{11}$.

For example, to measure the value of the point $S_{ref}(H)_{11}$, the constructor 24 performs a filtering operation 50 on the signal $S_m$, taking into account only the measurements made during the fraction $T_1$. For example, the operation is a synchronous demodulation operation. For this purpose, in a suboperation 52, each point of the signal $S_m$ during the fraction $T_1$ is multiplied by a corresponding point of a sinusoid of frequency $2f_H$. This sinusoid is phase-synchronized with the magnetic field $H_H$ via the link 25.

Next, in a suboperation 54, the result of each multiplication is accumulated in an accumulator.

At the end of the fraction $T_1$, in a suboperation 56, the result contained in the accumulator is divided by the number of results of multiplications added to one another. The result of this division is output by the constructor 24 as the value of the point $S_{ref}(H)_{11}$.

Next, the accumulator is reset and the suboperations 52 to 56 are executed for the values measured by the sensor 18 during the next fraction $T_2$.

Thus, the constructor 24 measures in succession the values of the points $S_{ref}(H)_{11}$ to $S_{ref}(H)_{1r}$.

Figure 3:
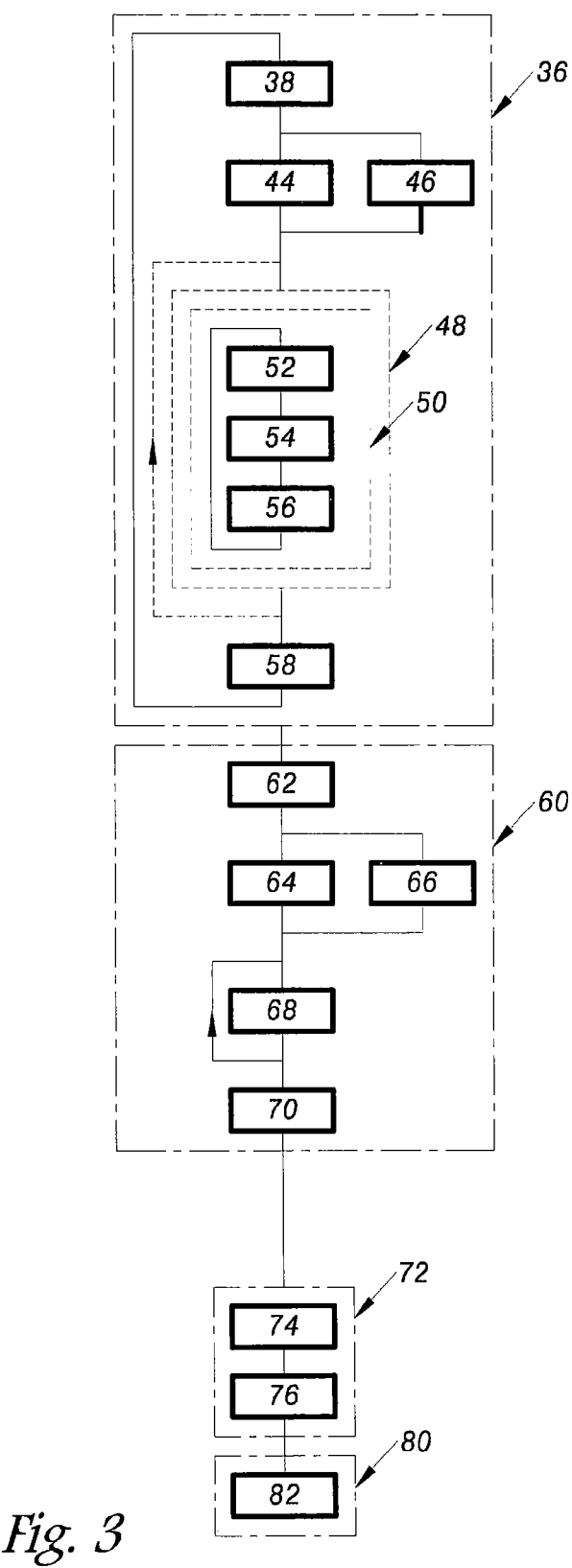
FIG. 3 is a flow chart for a method of analysing a magnetic material implemented in the analyser of FIG. 1.

Step 48 may be repeated over several successive periods $T_L$ of the low-frequency excitation magnetic field, as illustrated by the ascending dotted arrow (FIG. 3).

For example, it is assumed here that such is the case and that step 48 is repeated over N successive periods $T_L$. Thus, the signature $S_{ref}(H)_1$ comprises N×r points denoted by $S_{ref}(H)_{11}$ to $S_{ref}(H)_{1N \times r}$. N is advantageously greater than 1 and preferably greater than 10.

Next, in a step 58, the various points of the signature $S_{ref}(H)_1$ and the value of the mass $M_{ref1}$ are recorded in the memory 28.

Steps 38 to 58 are then repeated, the type 1 magnetic material being replaced with the type 2 magnetic material.

Thus, after the calibration phase 36, the memory 28 contains the signatures $S_{ref}(H)_1$ and $S_{ref}(H)_2$ and the reference masses $M_{ref1}$ and $M_{ref2}$.

A phase 60 of measuring an unknown mass of type 1 or type 2 magnetic material can then commence.

At the start of phase 60, in a step 62, an unknown mass of type 1 or type 2 magnetic material is placed in the receptacle 8. Next, steps 64, 66 and 68, which for example are identical to steps 44, 46 and 48 respectively, are carried out. Then, in a step 70, each time the constructor 24 constructs a new point $S(H)_P$ of the signature $S(H)$ this point is sent directly to the module 26. The suffix P represents the order number of the point in the signature.

The module 26 performs a phase 72 of automatically identifying the magnetic material placed in the receptacle 8.

Phase 72 starts with a step 74 of calculating two intercorrelation coefficients $\alpha_1$ and $\alpha_2$ using the following formulae:

$$\alpha_1 = \left[\sum_{P=1}^{Nr} S(H)_P S_{ref}(H)_{1P}\right] \bigg/ \sqrt{\sum_{P=1}^{Nr}(S(H)_P)^2 \sum_{P=1}^{Nr}(S_{ref}(H)_{1P})^2} \quad (3)$$

$$\alpha_2 = \left[\sum_{P=1}^{Nr} S(H)_P S_{ref}(H)_{2P}\right] \bigg/ \sqrt{\sum_{P=1}^{Nr}(S(H)_P)^2 \sum_{P=1}^{Nr}(S_{ref}(H)_{2P})^2} \quad (4)$$

Next, in a step 76, if the coefficient $\alpha_1$ is greater than the coefficient $\alpha_2$, then the magnetic material present in the receptacle 8 is identified as being a type 1 magnetic material. Conversely, if the coefficient $\alpha_1$ is less than the coefficient $\alpha_2$, then the magnetic material present in the receptacle 8 is identified as being a type 2 magnetic material.

It should be pointed out that the calculation of these intercorrelation coefficients involves the point-by-point multiplication of the signature $S(H)$ by the signature $S_{ref}(H)_1$ or $S_{ref}(H)_2$. This operation of multiplying the constructed signature by the reference signature obtained by measuring, under the same conditions, a reference mass of the same magnetic material, allows the noise added to the signature $S(H)$ to be very effectively eliminated. This therefore appreciably improves the sensitivity of the method of analysis.

This point-by-point multiplication appears here in the following term:

$$\sum_{P=1}^{Nr} S(H)_P S_{ref}(H)_{1P} \quad (5)$$

It will be assumed here that, during phase 72, the material to be analysed is identified as being a type 1 material.

Next, the module 26 performs a phase 80 of determining the mass of the magnetic material analysed.

At the start of phase 80, in a step 82, the module 26 determines the mass M of the magnetic material in the receptacle 8 by selecting the largest of the coefficients among $\alpha_1$ and $\alpha_2$ and then performing the following operation ($\alpha_1$ being the hypothesis):

$$M = \alpha_1 M_{ref1} \quad (6)$$

where:

$\alpha_1$ represents the intercorrelation coefficient of the signature $S(H)$ with the signature $S_{ref}(H)_1$ obtained in step 72;

$M_{ref1}$ represents the reference mass from which the signature $S_{ref}(H)_1$ was obtained; and M is the mass of the magnetic material analysed.

Here, use is therefore made of the property whereby the intercorrelation coefficient $\alpha_1$ is directly proportional to the ratio of the mass M to the mass $M_{ref1}$.

Figure 5:
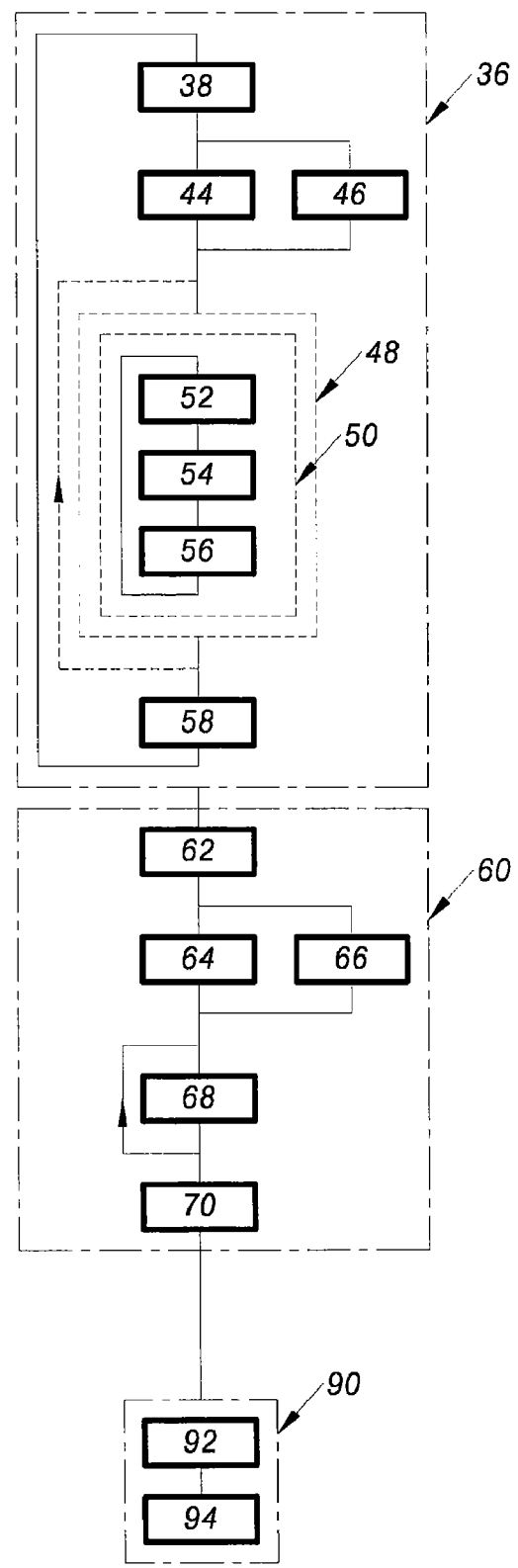
FIG. 5 is a flow chart for a method of analysing an assembly of different magnetic materials that can be implemented in the analyser of FIG. 1.

FIG. 5 shows a method of analysing an assembly of different magnetic materials that can be implemented in the analyser 2. Here, it is assumed that the assembly is formed from a mixture of type 1 and type 2 magnetic materials.

The method of FIG. 5 is identical to the method of FIG. 3 except that phases 72 and 80 are replaced with a phase 90 of identifying and simultaneously determining the mass of each of the magnetic materials present in the assembly.

At the start of phase 90, in a step 92, the module 26 determines the intercorrelation coefficients $\alpha_1$ and $\alpha_2$ by solving the following matrix equation:

$$\begin{bmatrix} S(H)_1 \\ S(H)_2 \\ \vdots \\ S(H)_P \end{bmatrix}^T = \begin{bmatrix} \alpha_1 \\ \alpha_2 \\ \vdots \\ \alpha_Q \end{bmatrix}^T \begin{bmatrix} S_{ref}(H)_{11} & \cdots & S_{ref}(H)_{1P} \\ S_{ref}(H)_{21} & \cdots & S_{ref}(H)_{2P} \\ \vdots & & \vdots \\ S_{ref}(H)_{Q1} & \cdots & S_{ref}(H)_{QP} \end{bmatrix} + \begin{bmatrix} N(H)_1 \\ N(H)_2 \\ \vdots \\ N(H)_P \end{bmatrix}^T \quad (7)$$

where:

$S(H)_j$ is the j-th point of the signature $S(H)$;

$\alpha_i$ is the ratio of the mass to be measured, of the magnetic material having the signature $S_{ref}(H)_i$, to the reference mass $M_{refi}$ used to construct the signature $S_{ref}(H)_i$;

$S_{ref}(H)_{ij}$ is the j-th point of the signature $S_{ref}(H)_i$;

$N(H)_j$ is the j-th point of a signal representative of the noise added to the measurement of the signature $S(H)$; and "$T$" is the symbol for the transpose function.

In this matrix equation (7), P represents the number of points contained in the signature $S(H)$, while Q represents the number of reference signatures. Thus, in the particular case described here, Q is equal to 2 and P is equal to Nr. In step 90, this matrix equation is for example solved using the pseudo-inverse method. This method gives the following solution to the above matrix equation:

$$\hat{V}_{1Q} = S(H)_{1P} S^T_{ref}(H)_{QP} (S_{ref}(H)_{QP} S^T_{ref}(H)_{QP})^{-1} \quad (8)$$

where:

$\hat{V}_{1Q}$ is the vector $[\alpha_1, \alpha_2, \ldots, \alpha_M]$;

$S(H)_{1P}$ is the vector $[S(H)_1, S(H)_2, S(H)_P]$;

$S_{ref}(H)_{QP}$ is the matrix of dimensions Q×P appearing in the matrix equation (7);

"$T$" is the transpose function; and

"$-1$" is the inverse function.

Next, in step 94, the mass $M_i$ of each of the magnetic materials present in the assembly contained in the receptacle 8 is determined using the following equation:

$$M_i = \alpha_i M_{refi} \quad (9)$$

where:

$M_{refi}$ is the reference mass used to establish the signature $S_{ref}(H)_i$ of the type i magnetic material.

Thus, the latter method has the advantage of allowing a mixture of several different magnetic materials, and therefore a mixture of several biological or chemical components, to be analysed simultaneously provided that the presence of each of the biological or chemical components is revealed by means of particles of magnetic materials different from those used to reveal the other biological or chemical components present in the same mixture.

In a first embodiment, a magnetic concentration is carried out, followed by the detection and/or quantification. Magnetic concentration or magnetic separation is a known technique consisting in concentrating the magnetic particles in a prescribed volume using magnetic fields. The magnetic material is functionalized by a ligand capable of binding the biological or chemical compound to be concentrated. If the component is a bacterium, the ligand may be an antibody or any other ligand capable of specifically binding to this bacterium. The ligands normally used are antibodies or biological macromolecules, such as hormones, and folic acid.

The magnetic concentration process may be a batch process, for example involving a magnet in contact with the receptacle containing the specimen, the magnet attracting and retaining the magnetic material and that which is bound thereto, in order to eliminate the liquid medium and other components possibly present. The magnetic concentration process may also be continuous, and for example involves a column or similar device, through which the liquid containing the magnetic material flows. The zone covered by the magnetic field is called the capture zone. This column or the like may contain, at least in this capture zone, a porous material. The magnetic field induces a strong gradient in the capture zone. The material retained can then be eluted.

This implementation of the invention with magnetic concentration may especially comprise:
- a first type of magnetic material, attached to which is a ligand capable of binding the biological or chemical component to be detected;
- the specimen to be analysed is mixed with said magnetic material, producing a magnetic material/component complex;
- the magnetic complex is magnetically concentrated, for example using a continuous or batch method as described above;
- said complex is then brought into contact with a different magnetic material, of a second type, attached to which is a ligand also capable of binding the biological or chemical component to be detected that is present on the magnetic material of the first type or of binding a reactant allowing this component to be detected and/or quantified; and
- the magnetic materials are analysed in order to deduce therefrom the mass of magnetic material of the second type and to deduce therefrom the presence or the quantity of biological or chemical component in the initial specimen.

In a second method of implementation, the invention is used to detect and/or quantify two or more biological or chemical components in the same specimen, using:
- a first type of magnetic material, which binds to a first biological or chemical component or to a reactant allowing this component to be detected and/or quantified; and
- at least one other, for example a second, different type of magnetic material, which binds to another, for example a second, biological or chemical component or to a reactant allowing this component to be detected and/or quantified, the implementation of the invention allowing each of these biological or chemical components to be detected and/or quantified separately.

This method of implementation may thus allow a biological specimen to be analysed for seeking and optionally quantifying several antigens of any one microorganism or of several microorganisms (of different nature or different type of the same microorganism, for example different serotypes of the same microorganism, e.g. a virus). It is also possible to analyse components of different nature simultaneously, for example an antibody and an antigen.

In a third method of implementation, which may be combined with the previous two, the invention is used to quantify at least one biological or chemical component in a specimen using a first type of magnetic material in the presence of a second, different, type of magnetic material, in which:
- the first type of magnetic material binds to the biological or chemical component to be quantified or to a reactant allowing this component to be detected and/or quantified; and
- the second type of magnetic material is inert with respect to the aforementioned component and preferably inert with respect to any component present in the specimen, the implementation of the invention allowing the masses of each of the types of magnetic material in the reaction zone to be quantified separately.

According to one feature of the invention, the second type of magnetic material serves as an internal reference, allowing the conditions under which the test is carried out to be taken into account, for example the diffusion characteristics either into or onto a porous material. This allows the test conditions to be taken into account so as to adjust the transposition of the mass of the first magnetic material, measured in the reaction zone, into a quantity of component in the specimen and to give a quantitative result independent of the conditions under which the test is carried out. For example, this makes it possible to compensate for the effects of variations in diffusion from one specimen to another. To do this, the total initial mass of the internal reference is determined and the mass measured in the reaction zone is compared to this total mass by making a ratio of the masses.

The analysis step of these various methods of implementation may be carried out in a conventional manner, after diffusion of the complex onto or into a porous support (e.g. a strip or miniature column) and specific retention of the complexes in a read zone. This method may also be adapted so as to concentrate and detect two or more components. The method according to the invention proves to be useful in the diagnostics and contaminant search fields. The specimens studied are those normally studied in these fields. They may come from body fluids, e.g. blood, plasma or urine, or may result from appropriate tissue treatment. The components sought may especially be antigens (microorganisms, e.g. bacteria, viruses, single-cell fungi, yeasts, parasites, or fractions thereof), antibodies or any other biological components, such as haptens, proteins, natural or synthetic oligonucleotides or polynucleotides, natural or synthetic monosaccharides, oligosaccharides or polysaccharides, lectins, avidin, streptavidin, biotin, growth factors, hormones, receptors and allergens. The invention is also suitable for searching and quantifying chemical entities or components such as antibiotics, narcotics, chemical contaminants, and allergens.

Examples of magnetic materials that can be used in such an implementation may include the aforementioned SeraMag® and MagPrep®.

Many other embodiments are possible. For example, the number of magnetic materials that can be identified or analysed simultaneously may be increased, by increasing the number of reference signatures contained in the memory 28. As a variant, the memory 28 may be reduced in size in the case in which it contains only a single signature, if the material to be analysed is always the same.

Here, the signatures were constructed by measuring the amplitude of the $2f_H$ frequency harmonic. As a variant, what has been described also applies to a signature constructed by measuring the amplitude of the $nf_H$ frequency harmonic where n is an integer equal to or greater than 1. However, preferably n will be strictly greater than 1 and preferably n will be even. This is because an even number allows the sensitivity to be even further improved compared with the case in which n is odd.

The magnetic material used may be of any appropriate type and exhibits a nonlinear magnetization characteristic.

For example magnetic particles can be typically from about 5 nm to about 50 μm in size, preferably from about 10 nm to about 10 μm, more preferably from about 100 nm to about 1 μm. The particles may have a spherical or ovoid shape, or any other shape. The particles may be made of the magnetic material itself or of a mixture of this material with a solid or semi-solid matrix. In the latter case, the magnetic material is dispersed in the matrix.

Figure 8:
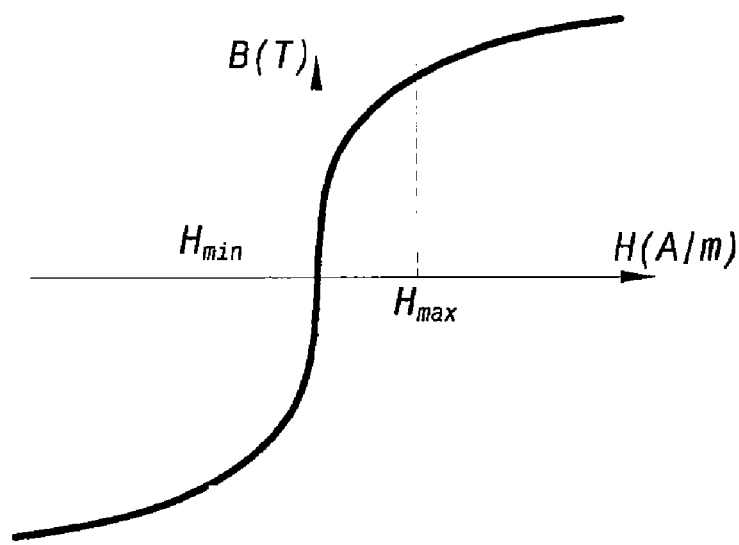
FIG. 8 is a graph representing the characteristic of the magnetic induction ($\vec{B}$) of a superparamagnetic material depending on the magnetic field ($\vec{H}$) applied to the material.

In an embodiment, the particles are superparamagnetic. In a feature, these particles are made of ferromagnetic elements in a matrix and the maximum dimension of the ferromagnetic elements is sufficiently small in order that each element taken individually has a magnetic cycle B(H) having the same properties than the one represented on FIG. 8. Typically, the maximum dimension of the ferromagnetic element is chosen to be below about 100 nm and generally below about 20 nm. This maximum dimension of the element below which the element becomes superparamagnetic depends on the ferromagnetic material used. The superparamagnetism as well as superparamagnetic elements are presented in E. du Trémolet de Lacheisserie and al. <<Magnétisme>> TOME 1, Presses Universitaire de Grenoble, 1999.

Iron oxides are the preferred superparamagnetic elements. To be more complete, it is specified that the element may be chosen among iron oxides and mixed oxides of iron and another metal, as a metal chosen among Mn, Ni, Zn, Bi, Cu, Co. $Fe_3O_4$ and $Fe_2O_3$ are preferred embodiments. Other examples include: perovskites with superparamagnetic properties, especially Fe-based perovskites; superparamagnetic nickel oxides, cobalt oxides or mixed oxides of these metals; as well as superparamagnetic metallic alloys, e.g. of the type FeNi or CoNi, especially $Fe_{20}Ni_{80}$.

In another embodiment, the particles are antiferromagnetic. An antiferromagnetic material is one where the spins of magnetic electrons align in a regular pattern with neighboring spins pointing in antiparallel directions. Such material include metals such as chromium, alloys such as FeMn, oxides such as NiO. Reference may also be made to E. du Trémolet de Lacheisserie and al. supra.

The solid or semi-solid matrix is chosen so as to not interfere with the magnetic properties of the element. In a feature, the matrix is diamagnetic.

Semi-solid matrix includes a matrix that is elastically deformable in a reversible manner, such as an elastomer.

Materials for the matrix include: natural, synthetic and artificial polymers, elastomers and gels, silica; for example plastic material, cellulosic material.

The distribution of the superparamagnetic elements in the matrix is such that the distances between the elements within the matrix are sufficient for the so-formed particles to have the same, or substantially the same, superparamagnetic properties than the element.

In another feature, the matrix allows the magnetic elements included in each particle to be close enough or mobile enough to magnetically interact together. This interaction may slightly impact the signature of the overall particle formed by the magnetic elements incorporated in the matrix, making it different from the signature of magnetic elements isolated. This phenomenon generates other candidates for multiplexing.

However, as a variant, any type of magnetic material may be used. In particular, the magnetic material may exhibit hysteresis or magnetic remanence. For example, the magnetic material may be a ferromagnetic or antiferromagnetic material.

The invention also provides for the use of template nanostructures to carry and/or contain magnetic particles.

The following description will mention several publications describing products and methods to produce the same that constitutes examples for carrying out the invention. The entire content of these publications is incorporated therein by reference and the person skilled in the art may use the methods described therein to implement the present invention.

Nanostructures have a predetermined shape. They may be chosen in particular among: nanotubes, nanowires, nanorings, nanodiscs, nanosprings. The nanostructure may be linear or not, opened or closed, two or three-dimensional. The nanostructure is deemed to develop a magnetic signature that is specific to the shape and size thereof, and the nature, amount and distribution of the magnetic material at the surface and/or within the nanostructure. Varying these factors allows the person skilled in the art to get different magnetic signatures as appropriate. Nanostructures may have a size from 50 nm up to >10 micrometers.

Nanostructures may be made of various materials, they may be metallic, such as carbon or copper, made of zirconia or may be peptidic, i.e. made of or comprising peptides, generally of histidine-rich peptide molecules, or lipidic, or heterolipidic, or a combination of above macromolecules.

Peptide nanostructures, such as nanotubes made by self-assembly of peptides have been described in S. Zhang et al., Current Opinion in Chemical Biology, 2002, 6:865-871; and M. Reches and E Gazit, Current Nanoscience, 2006, 2:105-111.

Zirconia nanotubes encapsulating metal nanowires have been described in J. Bao et al., Chem. Mater. 2002, 14:4709-4713. The procedure for preparing these nanotubes may be used herein to produce magnetic nanotubes by replacing the electrolyte $CuSO_4/H_3BO_3$ by an electrolyte comprising $FeCl_3$, $6H_2O$ and $NaBH_4$ (e.g. 20 g/L, respectively 50 g/L).

Another embodiment is the use of metallic nanostructures coated with peptides, such as the one described in I. A. Banerjee, PNAS 2003, 100, 25:14678-14682. This publication describes Cu nanocrystal growth on peptide nanotubes. This process may be modified to incorporate Fe in place of Cu. Fe may be brought for example using trimethylphosphinchloroiron salt.

When the nanostructure is to be used in an assembly according to the invention wherein detection thereof is necessary such as in a diagnosis method, said nanostructure including nanostructures coated with peptide may be functionalized to present a ligand moiety, for example an antibody or an antigen or a nucleic probe, or any useful chemical moiety, such as biotin.

Z. Zhao et al., J. Am. Chem. Soc., 2005, 127: 8939-8931, describes a method to coat nanostructures with antibodies, especially IgG.

The magnetic "particles" may also be magnetosomes or magnetosomes assemblies or aggregates. Magnetosomes are metallic oxide granules produced by magnetotactic bacteriae. They are formed of nanocrystals, especially monocrystalline, and generally surrounded by a lipidic biomembrane. Crystals have generally a size varying from 35 to 120 nm. They are mostly made of magnetite $Fe_3O_4$ and sometimes of greigite $Fe_3S_4$. Magnetite magnetosomes are a preferred embodiment.

Magnetosomes may be produced by cultivating a magnetotactic bacteria and extracting the magnetosomes. One example is cultivating *Magnetospirillum magneticum*, e.g. strain AMB-1. A method for cultivating this bacteria and extracting magnetosomes has been described in I. A. Banerjee et al., Adv. Mater., 2005, 17: 1128-1131. The bacteriae are grown anaerobically in a fermentor, the culture is harvested by centrifugation, disrupted and the magnetosomes are recovered using a magnet.

In a preferred embodiment, the magnetosomes are included in a nanostructure or attached to the surface of a nanostructure as described above. It is also possible to have the magnetosomes attached at the surface and included inside the nanostructure as well. As described above, the nanostructures have a predetermined shape, chosen in particular among: nanosprings. The nanostructure may be linear or not, opened or closed, two or three-dimensional.

An example of such nanostructure is described in Banerjee 2005. This publication describes the incorporation of the magnetosomes into nanotubes. This is an example of magnetic nanostructure useful in the invention.

What has been described here is also applicable to the identification and measurement of the mass of a solid block of magnetic materials.

In one embodiment, the invention is used for selectively sorting materials, for example plastics of different types, dispersed in the mass of which are magnetic materials according to the invention. Materials to be separated therefore incorporate from the beginning a magnetic material of a different type. For example, PVC packaging comprises a first type of magnetic material, while polyester packaging comprises a second type of magnetic material, and so on. By detecting the signature of a given material, it is possible to determine the material, for example packaging, and to separate it, manually or mechanically, from the other materials present.

If during the calibration phase the signal-to-noise ratio is high enough, the reference signature may be measured only over two periods $T_L$, the reference signature over a larger number of periods being able to be constructed from only these measurements.

If the form of the signature $S_{ref}(H)_i$ is already known, a single measurement during the calibration phase may be sufficient to construct a signature comprising several points.

Here, the method of analysis has been described in the particular case in which the measurements of the points of each signature $S_{ref}(H)_i$ and $S(H)$ are made for the same instantaneous values $H_{Li}$ of the magnetic field $H_L$. As a variant, the $H_{Li}$ values used to construct the signature $S_{ref}(H)_i$ may be different from the values $H_{Li}$ used to construct the signature $S(H)$. In that case, it is possible to construct the missing points of the signature $S_{ref}(H)_i$, corresponding to the points of the signature $S(H)$, by interpolation.

As a variant, it is possible to construct various signatures for the same magnetic material. For example, a first signature is constructed using the amplitude and the phase of a harmonic $xf_H$. A second signature for the same material is constructed using the amplitude and the phase of a harmonic $yf_H$, where x and y are non-zero integers differing from each other, and preferably equal to or greater than 2. Next, during the measurement of an unknown mass of this magnetic material, the two signatures may be used one after the other, or simultaneously. If the signatures are used simultaneously, this assumes that the constructor is capable of simultaneously extracting the amplitudes of the frequency harmonics $xf_H$ and $yf_H$. Next, the various intermediate masses obtained using the various signatures are combined to obtain the measured mass of the magnetic material. For example, the various intermediate masses are averaged.

An analysed magnetic material may be identified simply by comparing each intercorrelation coefficient $\alpha_i$ calculated at a predetermined threshold.

In the particular case in which the signatures $S_{ref}(H)_i$ are completely decorrelated, that is to say the intercorrelation coefficient $\beta$ between two signatures $S_{ref}(H)_i$ and $S_{ref}(H)_j$ is less than 0.1, it is possible to use the method of FIG. 3 to determine the mass of each magnetic material in an assembly of different magnetic materials. For this purpose, the method of FIG. 3 is repeated for each type of magnetic material sought, each time changing the reference signature.

If the various reference signatures are correlated, it is also possible to use the method of FIG. 3 to determine the mass of each of the magnetic materials of an assembly of different magnetic materials. For example, if the magnetic material is a mixture of type 1 and type 2 magnetic materials, the execution of the method of FIG. 3 using the reference signature $S_{ref}(H)_1$ then the signature $S_{ref}(H)_2$ amounts to the following system of equations:

$$\begin{cases} \alpha_{m1} = \alpha_1 + \alpha_2 \beta \\ \alpha_{m2} = \alpha_1 \beta + \alpha_2 \end{cases} \quad (10)$$

where:

$\alpha_{m1}$ and $\alpha_{m2}$ are the results obtained by applying equations (3) and (4) respectively;

$\alpha_1$ and $\alpha_2$ are equal to $$\frac{M_1}{M_{ref1}} \text{ and } \frac{M_2}{M_{ref2}}$$

respectively, where $M_1$ and $M_2$ are the respective masses of the type 1 and type 2 magnetic materials to be determined; and $\beta$ is the intercorrelation coefficient between the reference signatures $S_{ref}(H)_1$ and $S_{ref}(H)_2$.

Equation (10) allows the coefficients $\alpha_1$ and $\alpha_2$ to be determined and therefore the masses $M_1$ and $M_2$ to be determined.

As a variant, step 80 of the method of FIG. 3 may be omitted. In that case, the method of analysis makes it possible to identify only what the type of material present in the receptacle 8 is.

Conversely, if the type of magnetic material present in the receptacle 8 is known in advance, the identification phase 72 may be omitted. In this variant, the calculation of the intercorrelation coefficient $\alpha_i$ between the signature $S(H)$ and the reference signature $S_{ref}(H)_i$ will be carried out during phase 80 before step 82. In this variant, the number r of period fractions may be reduced to two.

The methods of FIGS. 3 and 5 have been described in the particular case in which, during the calculation of the intercorrelation coefficient $\alpha_i$, the signatures $S(H)$ and $S_{ref}(H)_i$ are multiplied together point by point. However, as a variant, the signatures $S(H)$ and $S_{ref}(H)_i$ may be multiplied point by point with a third reference signature $S_{ref}(H)_K$. In that case, the mass $M_1$ of a type 1 magnetic material present in the receptacle 8 is calculated using the following equations:

$$\beta_1 = \frac{\left[\sum_{P=1}^{Nr} S_{ref}(H)_{1P} S_{ref}(H)_{KP}\right]}{\sqrt{\sum_{P=1}^{Nr} (S_{ref}(H)_{1P})^2 \sum_{P=1}^{Nr} (S_{ref}(H)_{KP})^2}} \quad (11)$$

$$\alpha_1 = \frac{\left[\sum_{P=1}^{Nr} S(H)_P S_{ref}(H)_{KP}\right]}{\sqrt{\sum_{P=1}^{Nr} (S(H)_P)^2 \sum_{P=1}^{Nr} (S_{ref}(H)_{KP})^2}} \quad (12)$$

$$M_1 = (\alpha_1 M_{ref1})/\beta_1 \quad (13)$$

where:
- $\beta_1$ is the intercorrelation coefficient between the reference signature $S_{ref}(H)_1$ of the type 1 magnetic material and the reference signature $S_{ref}(H)_K$; and
- $\alpha_1$ is the intercorrelation coefficient between the measured signature $S(H)$ and the reference signature $S_{ref}(H)_K$.

The signature $S_{ref}(H)_K$ may be the signature measured on a magnetic material different from the type 1 magnetic material. The signature $S_{ref}(H)_K$ may also be any signature chosen by the designers of the analyser 2.

For example, the signature $S_{ref}(H)_K$ may be a series of pseudo-random points. This variant therefore makes it possible to record only a single reference signature $S_{ref}(H)_K$. However, the memory 28 must also contain the intercorrelation coefficient $\beta_i$ between each reference signature $S_{ref}(H)_i$ and this signature $S_{ref}(H)_K$.

In another embodiment, it is possible to use several reference signatures obtained for various reference masses of the same magnetic material. For example, it is assumed that the signature $S_{ref}(H)_K$, described with regard to equations (11) and (12), is used as reference signature. For the reference masses $M_{ref11}$ and $M_{ref12}$ of the type 1 magnetic material, equation (11) gives the results $\beta_{11}$ and $\beta_{12}$. It is also assumed that equation (12) gives the result $\alpha_1$ lying between $\beta_{11}$ and $\beta_{12}$. The mass $M_1$ of type 1 material in the receptacle 8 can then be calculated using the following equation:

$$M_1 = [M_{ref1}(\beta_{12} - \alpha_1) + M_{ref2}(\alpha_1 - \beta_{11})]/(\beta_{12} - \beta_{11}) \quad (14)$$

The mass $M_1$ is therefore obtained by linear interpolation between the masses $M_{ref1}$ and $M_{ref2}$. It will therefore be understood that using several signatures for the same magnetic material allows the precision to be improved, especially if the equation between mass $M_1$ and coefficient $\alpha_1$ is not linear.

Figure 6:
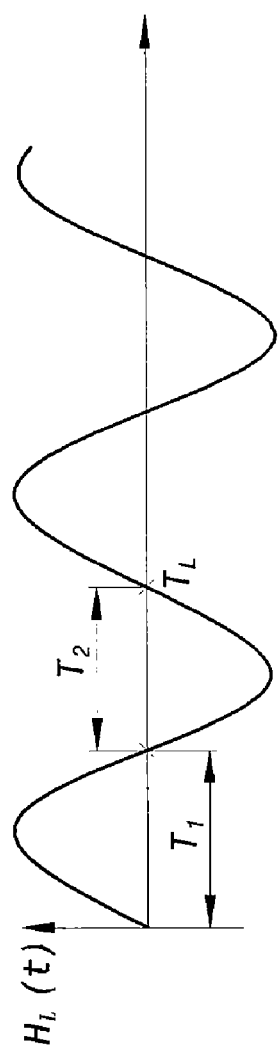
FIGS. 6 and 7 are timing diagrams illustrating various waveforms for a low-frequency magnetic field that can be implemented in the analyser of FIG. 1.

The analyser 2 has been described in the particular case in which the magnetic field $H_L$ is constant over each of the fractions $T_P$. As a variant, the instantaneous value of the magnetic field $H_L$ is not constant over each of the fractions $T_P$. However, the averages of the instantaneous value of the magnetic field $H_L$ over each of the fractions $T_P$ are different from one another. For example, as shown in FIG. 6, the instantaneous value of the magnetic field $H_L$ as a function of time may be a sinusoid. It may be confirmed that the average of the instantaneous value over the fraction $T_1$ is indeed different from the average of the instantaneous value over the fraction $T_2$.

Figure 7:
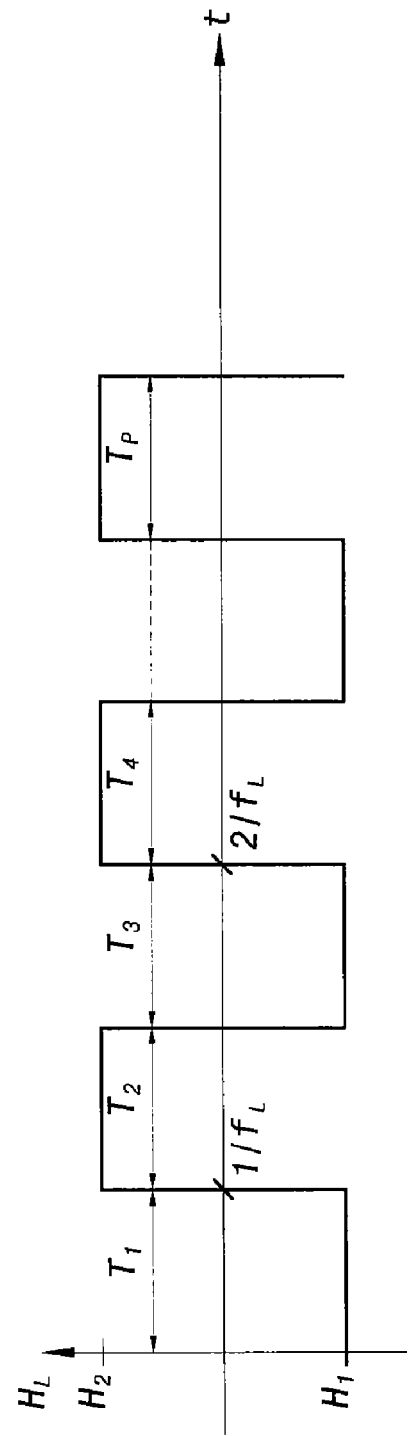

Each period $T_L$ of the low-frequency excitation magnetic field may be divided into more than two fractions. For example, FIG. 7 shows the variation over the course of time of the instantaneous value of a low-frequency magnetic field in which each period $T_L$ is divided into s fractions, where s is strictly greater than two.

However, each period fraction must be long enough to allow the constructor 24 to measure the point $S(H)_{ij}$. For this purpose, each period fraction here lasts at least 100 nanoseconds, and preferably at least 1 µs.

Finally, the generator 12 may be replaced with two independent excitation magnetic field generators. The first of these generators is controlled so as to generate only the magnetic field $H_L$, while the second of these generators is controlled so as to generate only the magnetic field $H_H$. For example, at least one of these independent generators is produced using a magnet or a coil supplied with direct current, said magnet or coil being moved close to the magnetic material to be analysed so as to generate the field $H_L$ or the field $H_H$.

The invention claimed is:

1. A method of analysing a magnetic material, comprising:
   a) excitation of the magnetic material simultaneously with:
      a low-frequency excitation magnetic field ($H_L$) of periods $T_L$, the period $T_L$ comprising at least first and second period fractions such that the average of the instantaneous value of the low-frequency magnetic field over the first period fraction is different from the average of its instantaneous value over the second period fraction, each period fraction having a duration of at least 100 nanoseconds and
      a high-frequency excitation magnetic field ($H_H$), the variation of the instantaneous value of which over the course of time is periodic with a frequency $f_H$, the frequency $f_H$ of the high-frequency excitation magnetic field being at least twice the frequency $f_L$ of the low-frequency magnetic field;
   b) the construction of a signature $S(H)$ of the magnetic material formed from at least two points $S(H)_P$, this construction including obtaining the value of each point $S(H)_P$ by measuring, over each period fraction, the amplitude and possibly the phase of a harmonic of the magnetic field induced in the magnetic material, said amplitude and phase being obtained in response to the excitation during this period fraction, the harmonic having a frequency $nf_H$, where n is a non-zero positive integer; and
   c) the identification and/or the determination of the mass of the magnetic material from several points of the constructed signature $S(H)$.

2. The method according to claim 1, in which it includes the automatic identification of the magnetic material as a function of the result of the correlation of the signature $S(H)$ with each of the reference signatures $S_{ref}(H)_i$ of a set of several reference signatures, each reference signature $S_{ref}(H)_i$ having been obtained with a magnetic material different from the other magnetic materials used to obtain the other reference signatures, first and second magnetic materials being considered as different from each other if an intercorrelation coefficient $\beta$ defined by the following equation is less than 0.95:

$$\beta = \frac{\left[\oint_H \frac{d^n B(H)_1}{dH^n} \frac{d^n B(H)_2}{dH^n} dH\right]}{\sqrt{\left(\oint_H \left(\frac{d^n B(H)_1}{dH^n}\right)^2 dH\right)\left(\oint_H \left(\frac{d^n B(H)_2}{dH^n}\right)^2 dH\right)}}$$

where:

$$-\frac{d^n B(H)_1}{dH^n} \text{ and } \frac{d^n B(H)_2}{dH^n}$$

are the n-th derivatives of the magnetic induction with respect to the magnetic field of the first and second magnetic materials respectively, n being the same number as that defining the harmonic of frequency $nf_H$; and $$-\oint_H dH$$

indicates that the integration is carried out, in the same manner for both the first and second magnetic materials, by circulation over a closed path, describing a cycle starting from $H_{min}$, passing through $H_{max}$ and returning to $H_{min}$, where $H_{min}$ and $H_{max}$ are the minimum and maximum of the excitation magnetic field respectively.

3. The method according to claim 1, in which the determination of the mass comprises:
the multiplication of several points of the signature S(H) with, respectively, each corresponding point of a reference signature $S_{ref}(H)_i$ measured under the same conditions on a reference mass of the same magnetic material; and
the calculation of the mass of the magnetic material as a function of the result of this multiplication.

4. The method according to claim 1, in which the identification and/or the determination of the mass of the magnetic material are/is also carried out on the basis of at least one reference signature $S_{ref}(H)_i$ measured under the same conditions on a reference mass of the same magnetic material.

5. The method according to claim 1, applied to the analysis of an assembly of several different magnetic materials, first and second magnetic materials being considered as different from each other if an intercorrelation coefficient $\beta$ defined by the following equation is less than 0.95:

$$\beta = \frac{\left[\oint_H \frac{d^n B(H)_1}{dH^n} \frac{d^n B(H)_2}{dH^n} dH\right]}{\sqrt{\left(\oint_H \left(\frac{d^n B(H)_1}{dH^n}\right)^2 dH\right)\left(\oint_H \left(\frac{d^n B(H)_2}{dH^n}\right)^2 dH\right)}}$$

where:

$$-\frac{d^n B(H)_1}{dH^n} \text{ and } \frac{d^n B(H)_2}{dH^n}$$

are the n-th derivatives of the magnetic induction with respect to the magnetic field of the first and second magnetic materials respectively, n being a non-zero positive integer; and $$-\oint_H dH$$

indicates that the integration is carried out, in the same manner for both the first and second magnetic materials, by circulation over a closed path, describing a cycle starting from $H_{min}$, passing through $H_{max}$ and returning to $H_{min}$, where $H_{min}$ and $H_{max}$ are the minimum and maximum of the excitation magnetic field respectively, in which the identification and/or the determination consist/consists in identifying and/or determining the mass of at least one of the magnetic materials of the assembly on the basis of several points of the signature S(H) and of several signatures $S_{ref}(H)_i$, each measured under the same conditions on a reference mass of each of the magnetic materials of the assembly.

6. The method according to claim 5, in which the determination of the masses of each of the magnetic materials in the assembly of magnetic materials comprises the solution of the following matrix equation:

$$\begin{bmatrix} S(H)_1 \\ S(H)_2 \\ \vdots \\ S(H)_P \end{bmatrix}^T = \begin{bmatrix} \alpha_1 \\ \alpha_2 \\ \vdots \\ \alpha_Q \end{bmatrix}^T \begin{bmatrix} S_{ref}(H)_{11} & \cdots & S_{ref}(H)_{1P} \\ S_{ref}(H)_{21} & \cdots & S_{ref}(H)_{2P} \\ \vdots & & \vdots \\ S_{ref}(H)_{Q1} & \cdots & S_{ref}(H)_{QP} \end{bmatrix} + \begin{bmatrix} N(H)_1 \\ N(H)_2 \\ \vdots \\ N(H)_P \end{bmatrix}^T$$

where:
Q is the number of reference signatures, Q being equal to or greater than the number of different magnetic materials present in the assembly;
P is the number of points of each signature, P being equal to or greater than two;
$S(H)_j$ is the j-th point of the signature S(H);
$\alpha_i$ is the ratio of the mass to be measured, of the magnetic material having the signature $S_{ref}(H)_i$, to the reference mass used to construct the signature $S_{ref}(H)_i$;
$S_{ref}(H)_{ij}$ is the j-th point of the signature $S_{ref}(H)_i$;
$N(H)_j$ is the j-th point of a signal representative of the noise added to the measurement of the signature S(H); and
"$T$" is the symbol for the transpose function.

7. The method according to claim 1, in which the instantaneous value of the low-frequency magnetic field during each of the period fractions is constant.

8. The method according to claim 1, applied to the detection or quantification of a biological or chemical component in a specimen, in which method the assembly is obtained in the following manner:
a first magnetic material, attached to which is a ligand capable of binding the biological or chemical component to be detected, is mixed with the specimen to be analysed, producing a magnetic material/component complex;
the magnetic complex is concentrated in a prescribed volume using a magnetic field;
this complex is then brought into contact with a second, different, magnetic material, attached to which is a ligand also capable of binding the same biological or chemical component to be detected that is present on the first material or to a reactant allowing this component to be detected and/or quantified;
the analysis of the assembly of magnetic materials thus obtained allowing the detection and/or the quantification of said component.

9. The method according to claim 5, applied to the detection or quantification of at least two biological or chemical components in a specimen, in which method the assembly is obtained mixing the specimen:
with a first magnetic material, which binds to a first biological or chemical component or to a reactant allowing this component to be detected and/or quantified;

and with a second, different, magnetic material, which binds to a second biological or chemical component or to a reactant allowing this component to be detected and/or quantified.

10. The method according to claim 5, applied to the detection or quantification of at least two biological or chemical components in a specimen, in which method the assembly is obtained by mixing the specimen:
- with a first magnetic material, which binds to the biological or chemical component or to a reactant allowing this component to be detected and/or quantified; and
- with a second, different, magnetic material, which is inert with respect to the aforementioned component.

11. A device for analysing a magnetic material, comprising:
- a) a generator designed to excite the magnetic material simultaneously with:
  - a low-frequency excitation magnetic field ($H_L$) of periods $T_L$, the period $T_L$ comprising at least first and second period fractions such that the average of the instantaneous value of the low-frequency magnetic field over the first period fraction is different from the average of its instantaneous value over the second period fraction, each period fraction having a duration of at least 100 nanoseconds and
  - a high-frequency excitation magnetic field ($H_H$), the variation of its instantaneous value of which over the course of time is periodic with a frequency $f_H$, the frequency $f_H$ of the high-frequency excitation magnetic field being at least two times the frequency $f_L$ of the low-frequency magnetic field;
- b) a signature constructor for constructing a signature $S(H)$ of the magnetic material formed from at least two points $S(H)_P$, this constructor being capable of obtaining the value of each point $S(H)_P$ by measuring, over each period fraction, the amplitude and possibly the phase of a harmonic of the magnetic field induced in the magnetic material, said amplitude and phase being obtained in response only to the excitation during this period fraction, the harmonic having a frequency $nf_H$, where n is a non-zero positive integer; and
- c) a module for identifying and/or determining the mass of the magnetic material on the basis of several of the points of the constructed signature $S(H)$.

12. The device according to claim 8, applied to the analysis of an assembly of several different magnetic materials, first and second magnetic materials being considered as different from each other if an intercorrelation coefficient β defined by the following equation is less than 0.95:

$$\beta = \frac{\left[\oint_H \frac{d^n B(H)_1}{dH^n} \frac{d^n B(H)_2}{dH^n} dH\right]}{\sqrt{\left(\oint_H \left(\frac{d^n B(H)_1}{dH^n}\right)^2 dH\right)\left(\oint_H \left(\frac{d^n B(H)_2}{dH^n}\right)^2 dH\right)}}$$

where:

$$\frac{d^n B(H)_1}{dH^n} \text{ and } \frac{d^n B(H)_2}{dH^n}$$

are the n-th derivatives of the magnetic induction with respect to the magnetic field of the first and second magnetic materials respectively, n being a non-zero positive integer; and $$-\oint_H dH$$

indicates that the integration is carried out, in the same manner for both the first and second magnetic materials, by circulation over a closed path, describing a cycle starting from $H_{min}$, passing through $H_{max}$ and returning to $H_{min}$, where $H_{min}$ and $H_{max}$ are the minimum and maximum of the excitation magnetic field respectively, in which an identification and/or determination module is capable of identifying and/or determining the mass of at least one of the magnetic materials of the assembly on the basis of several of the points of the constructed signature $S(H)$ and of several signatures $S_{ref}(H)_i$, each measured under the same conditions on a reference mass of each of the magnetic materials of the assembly.

13. An analyser for analysing an analysis medium that may contain at least one biological and/or chemical component, the medium to be analysed including magnetic particles bound to the component or to a reactant allowing the component to be detected and/or quantified, this analyser comprising:
- a receptacle suitable for containing the analysis medium; and
- a device in accordance with claim 8 for measuring the mass of the ensemble of magnetic particles present in the analysis medium, the result of this measurement being proportional to the quantity of component to be analysed that is present in the analysis medium.

14. An analyser according to claim 13, for analysing an analysis medium containing at least two different magnetic materials.

15. The analyser according to claim 14, for implementing a method of analysing a magnetic material comprising:
- a) excitation of the magnetic material simultaneously with:
  - a low-frequency excitation magnetic field ($H_L$) of periods $T_L$, the period $T_L$ comprising at least first and second period fractions such that the average of the instantaneous value of the low-frequency magnetic field over the first period fraction is different from the average of its instantaneous value over the second period fraction, each period fraction having a duration of at least 100 nanoseconds and
  - a high-frequency excitation magnetic field ($H_H$), the variation of the instantaneous value of which over the course of time is periodic with a frequency $f_H$, the frequency $f_H$ of the high-frequency excitation magnetic field being at least twice the frequency $f_L$ of the low-frequency magnetic field;
- b) the construction of a signature $S(H)$ of the magnetic material formed from at least two points $S(H)_P$, this construction including obtaining the value of each point $S(H)_P$ by measuring, over each period fraction, the amplitude and possibly the phase of a harmonic of the magnetic field induced in the magnetic material, said amplitude and phase being obtained in response to the excitation during this period fraction, the harmonic having a frequency $nf_H$, where n is a non-zero positive integer; and
- c) the identification and/or the determination of the mass of the magnetic material from several points of the constructed signature $S(H)$,
- wherein the method is applied to the detection or quantification of a biological or chemical component in a specimen, in which method the assembly is obtained in the following manner:

a first magnetic material, attached to which is a ligand capable of binding the biological or chemical component to be detected, is mixed with the specimen to be analysed, producing a magnetic material/component complex;

the magnetic complex is concentrated in a prescribed volume using a magnetic field;

this complex is then brought into contact with a second, different, magnetic material, attached to which is a ligand also capable of binding the same biological or chemical component to be detected that is present on the first material or to a reactant allowing this component to be detected and/or quantified; and the analysis of the assembly of magnetic materials thus obtained allowing the detection and/or the quantification of said component.

16. The method according to claim 6, applied to the detection or quantification of at least two biological or chemical components in a specimen, in which method the assembly is obtained mixing the specimen:

with a first magnetic material, which binds to a first biological or chemical component or to a reactant allowing this component to be detected and/or quantified;

and with a second, different, magnetic material, which binds to a second biological or chemical component or to a reactant allowing this component to be detected and/or quantified.

17. The method according to claim 6, applied to the detection or quantification of at least two biological or chemical components in a specimen, in which method the assembly is obtained by mixing the specimen:

with a first magnetic material, which binds to the biological or chemical component or to a reactant allowing this component to be detected and/or quantified; and with a second, different, magnetic material, which is inert with respect to the aforementioned component.

18. An analyser for analysing an analysis medium that may contain at least one biological and/or chemical component, the medium to be analysed including magnetic particles bound to the component or to a reactant allowing the component to be detected and/or quantified, this analyser comprising:

a receptacle suitable for containing the analysis medium; and a device in accordance with claim 9 for measuring the mass of the ensemble of magnetic particles present in the analysis medium, the result of this measurement being proportional to the quantity of component to be analysed that is present in the analysis medium.

19. An analyser according to claim 18, for analysing an analysis medium containing at least two different magnetic materials.

* * * * *